United States Patent [19]

Stien

[11] Patent Number: 4,884,968
[45] Date of Patent: Dec. 5, 1989

[54] PROTECTIVE DEVICE FOR DENTIST HANDPIECE

[76] Inventor: Jerome A. Stien, 32 Stagecoach La., Newington, Conn. 06111

[21] Appl. No.: 189,219

[22] Filed: May 2, 1988

[51] Int. Cl.$^4$ ............................................. A61C 1/16
[52] U.S. Cl. .................................................. 433/116
[58] Field of Search ........................................ 433/116

[56] References Cited

U.S. PATENT DOCUMENTS

| | | | |
|---|---|---|---|
| 1,516,933 | 11/1924 | Terranova | 433/116 X |
| 2,835,084 | 5/1958 | Fotre | 433/116 X |
| 2,924,013 | 2/1960 | Wowra | 433/116 |
| 4,286,950 | 9/1981 | Hawk | 433/116 |
| 4,424,036 | 1/1984 | Lokken | 433/116 |
| 4,789,336 | 12/1988 | Lewis | 433/116 |

Primary Examiner—Robert P. Swiatek
Assistant Examiner—Nicholas D. Lucchesi
Attorney, Agent, or Firm—McCormick, Paulding & Huber

[57] ABSTRACT

A shield for a dentist's handpiece slips on over the head and has a skirt portion that protects the user from injury due to the bit or bur.

4 Claims, 1 Drawing Sheet

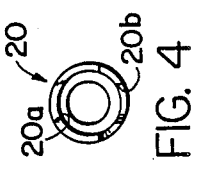
FIG. 4
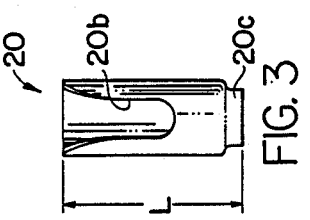
FIG. 3
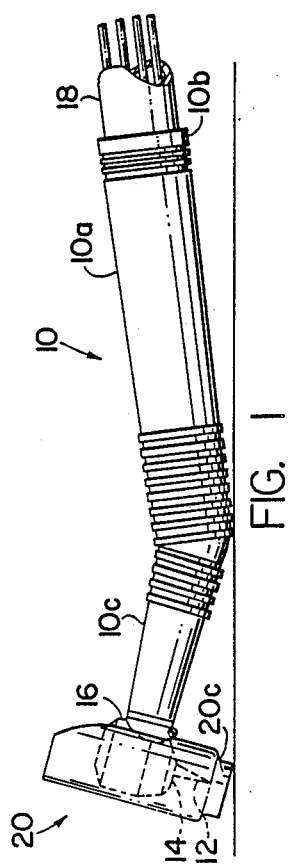
FIG. 1
FIG. 2

PROTECTIVE DEVICE FOR DENTIST HANDPIECE

This invention relates generally to the handpiece commonly used by dentists for rotatably supporting a bit or bur such that the dentist can manipulate the tool while working in the patient's mouth to repair his teeth. The dentist's handpiece comprises only one of several tools the dentist will commonly need in connection with performing the variety of jobs commonly required on a particular patient. Thus, the dentist will commonly set down his handpiece and pick up another tool, while at the same time concentrating on the job at hand. When the dentist decides once again to pick up the handpiece or another nearby tool he is apt to cut himself on the bit or bur in the course of reaching for or over the handpiece. This poses a definite hazard to the dentist since the handpiece will normally lie on a flat surface with the bit or bur projecting from the head of the handpiece. This bit or bur is quite sharp and being of such small size will often cause injury to the dentist's hand or other parts of his body as a result of its peculiar geometry.

The general purpose of the present invention is to provide a protective device or shield for the bit or bur in such a handpiece, and in its presently preferred form such a shield comprises a generally cylindrical or tubular plastic element fabricated of such a size so as to be slidably received on the head of the handpiece and of such a length that the tubular shield includes a depending skirt surrounding the bit or bur. The shield is of annular cross section throughout its length and preferably tapers to define a small opening at the end associated with the end of the bit or bur commonly provided in a typical handpiece. The generally tubular shield preferably includes a slot it its side wall to receive the support arm or handle portion of the handpiece and this slot permits the shield to be received on the head so that the shield completely encloses the head thereby permitting the shield to be held in place solely as a result of the friction provided between the interior surface of the shield and the exterior cylindrical surface of the head.

Another feature of the present invention is that such a shield can be color coded to identify the type of bit or bur that is provided in the handpiece chuck or head.

FIG. 1 is a side elevational view of a typical dentist's handpiece illustrating a shield constructed in accordance with the present invention.

FIG. 2 is a perspective view of the handpiece illustrated in FIG. 1 with the handpiece omitted.

FIG. 3 is an elevational view of the shield illustrated in FIGS. 1 and 2.

FIG. 4 is a top plan view of the shield.

Turning now to the drawings in greater detail, and referring initially to FIG. 1, a dentist's handpiece is illustrated generally at 10, and this handpiece includes a portion 10a adapted to be gripped by the dentist so as to permit the dentist to manipulate a bit or bur 12 provided in a chuck 14 rotatably mounted in a head portion 16 of the handpiece. The handpiece may also include an end portion 10b to permit the portion 10a to be rotated without necessarily incurring a countertorque from the cable or supply conduit that delivers the air for rotating an internal impeller (not shown) associated with the chuck 14 so as to rotate the bit or bur 12, and which cable or conduit 18 may also include other lines such as water and air or vacuum lines as is characteristic of present day dentist's handpieces generally.

As described above the handpiece 10 is of generally conventional configuration and in accordance with the present invention this handpiece 10 is provided with a protective shield 20 of sufficient length L so as to equal or exceed the combined length of the head 16 and exposed portion of the drill bit or bur 12.

The tubular shield 20 is preferably fabricated from an expendable or inexpensive thermoplastic material such as polyethylene or polyvinylchloride and as best shown in FIG. 2 the shield 20 includes an upper generally cylindrical portion defining an opening 20a that is sized so as to snuggly receive the generally cylindrical head portion 16 of the handpiece 10. A slot 20b is also provided so that the sleeve can be provided on the head 16 in such a way that the upper end of the sleeve extends above the upper end of the cylindrical head portion 16. The slot 20b accommodates the portion 10c of the handle 10a. The length L of the shield 20 is preferably such that it extends well beyond the top of the head 16 to facilitate removal of the shield. The slot 20b snuggly engages the arm 10c to frictionally retain the shield on the head.

As best shown in FIGS. 1 and 2 the tubular sleeve 20 projects above the head, but also includes a depending skirt portion 20c that surrounds the bit or bur 12 to protect the dentist and anyone coming into contact with the handpiece 10 from injury due to the relatively sharp and quite small bit or bur 12. As shown in FIG. 3 the depending skirt portion 20c may be of reduced diameter to further protect those coming in contact with the handpiece and its bit or bur 12. This shield 20 also protects the condition of the bit or bur 12 when the handpiece is not actually being used by the dentist.

In further accordance with the present invention a plurality of such shields are preferably provided, with a color coded band (not shown) that serves to identify the bit or bur then being used in the handpiece 10 and facilitates the dentist in identifying a particular bit or bur. This will help him to avoid using a bit or bur that should have been replaced with another, or to identify the bit or bur in the handpiece after the handpiece has been laid down for some reason and is to be picked up again for reuse by the dentist. With a plurality of such shields provided in color coded sets the particular bit or bur configurations can be identified when these bits or burs are provided in the dentist's handpieces.

I claim:

1. In combination with a dentist's handpiece of the type that includes a handle portion and a generally cylindrical head portion provided perpendicularly to the handle, and wherein the head includes a chuck for receiving a dentist's bit or bur, said bur projecting beyond the head and being rotatable on the axis or centerline of the head, a protective shield for the bit or bur, said shield having a substantially cylindrical shape with an upper annular edge and snuggly receiving said head, and said shield having an annular cross section that defines a depending skirt surrounding the bit or bur, said shield fabricated from a plastic material so that said shield is frictionally retained on the head by engagement between the inner cylindrical surface of the shield and the outer cylindrical surface of the head, said shield including a slot upwardly open in said upper annular edge and terminating at a location above a lower edge of said shield, said slot being of such a width as to snuggly receive the handle portion of the handpiece, and said slot having an inner end that abuts the handle to define a position for the shield such that the depending skirt surrounding the bit or bur extends beyond the end of the bit or bur.

2. The combination of claim 1 above wherein said shield also includes an upwardly projecting portion extending above the top of the dentist's handpiece head portion in order to facilitate removal of the shield from the handpiece.

3. The combination of claim 2 wherein said depending skirt portion of said shield has an annular cross section that reduces in diameter so as to define a smaller opening at the end opposite said head receiving end thereof.

4. The combination of claim 3 further characterized by a plurality of such shields, said shields being provided in color coded sets to identify bits or burs of different types adapted for selective use on said dentist's handpiece.

* * * * *